United States Patent
Tuysuzoglu et al.

(10) Patent No.: US 11,698,380 B2
(45) Date of Patent: Jul. 11, 2023

(54) OPTIMIZATION-BASED LOAD PLANNING SYSTEMS AND METHODS FOR LABORATORY ANALYZERS

(71) Applicant: Siemens Healthcare Diagnostics Inc., Tarrytown, NY (US)

(72) Inventors: Ahmet Tuysuzoglu, Jersey City, NJ (US); Yue Zhang, Jersey City, NJ (US); Michael Heydlauf, Cary, NC (US); Luxi Zheng, Cary, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/597,452

(22) PCT Filed: Jun. 1, 2020

(86) PCT No.: PCT/US2020/035507
§ 371 (c)(1),
(2) Date: Jan. 6, 2022

(87) PCT Pub. No.: WO2021/015854
PCT Pub. Date: Jan. 28, 2021

(65) Prior Publication Data
US 2022/0214368 A1    Jul. 7, 2022

Related U.S. Application Data (60) Provisional application No. 62/877,885, filed on Jul. 24, 2019.

(51) Int. Cl.
  *G01N 35/00* (2006.01)
  *G16H 40/67* (2018.01)
  (Continued)

(52) U.S. Cl.
  CPC ... *G01N 35/0092* (2013.01); *G01N 35/00613* (2013.01); *G01N 35/00871* (2013.01);
  (Continued)

(58) Field of Classification Search
  CPC ............ G01N 35/02; G01N 35/10; G01N 2035/00049; G01N 2203/0208;
  (Continued)

(56) References Cited

U.S. PATENT DOCUMENTS 8,024,395 B1 * 9/2011 Odom ............ H04L 47/78
709/201
10,139,422 B2 * 11/2018 Pollack .......... G01N 35/0095
(Continued)

FOREIGN PATENT DOCUMENTS

WO    2018022351    2/2018
WO    2018022474    2/2018
(Continued)

OTHER PUBLICATIONS

International Search Report for PCT/US2020/035507 dated Sep. 8, 2020.
(Continued)

*Primary Examiner* — Shogo Sasaki (57) ABSTRACT

Systems and methods include an optimization-based load planning module for laboratory analyzers of bio-fluid samples. The optimization-based load planning module is executable on a computer server and is configured to optimize assay (lab test) assignments across a large number of laboratory analyzers based on one or more of the following user selected and weighted objectives: reduced turn-around-time, load balancing, efficient reagent usage, lower quality assurance costs, and/or improved system robustness. The optimization-based load planning module outputs a load plan comprising computer executable instructions config-
(Continued)

ured to cause a system controller of a laboratory analyzer system to schedule and direct each requested test to be performed at one or more selected laboratory analyzers of the laboratory analyzer system in accordance with the user selected and weighted objectives. Other aspects are also described.

20 Claims, 4 Drawing Sheets

(51) Int. Cl.
*G16H 10/40* (2018.01)
*G16H 40/40* (2018.01)

(52) U.S. Cl.
CPC ............. *G16H 10/40* (2018.01); *G16H 40/40* (2018.01); *G16H 40/67* (2018.01); *G01N 2035/0094* (2013.01); *G01N 2035/00881* (2013.01)

(58) Field of Classification Search
CPC ....... G01N 2293/904; G01N 2223/305; G01N 2223/3068; B01L 3/54; B01L 2200/14; B01L 2200/143; B01L 2200/16; B01L 2300/0233; G05B 2219/2657; G05B 2249/32247; G05B 2219/34418; G05B 2219/33334; G05B 2219/32388; G06F 11/3433; G06F 2206/1012; H04L 67/1031; H04L 47/726; H04L 2012/568
See application file for complete search history.

(56) References Cited

U.S. PATENT DOCUMENTS

| | | | |
|---|---|---|---|
| 2005/0227360 A1 | 10/2005 | Devlin, Sr. | |
| 2008/0215409 A1* | 9/2008 | Van Matre | G06Q 10/0631 705/7.12 |
| 2008/0235055 A1 | 9/2008 | Mattingly et al. | |
| 2009/0109230 A1 | 4/2009 | Miller et al. | |
| 2009/1019230 | 4/2009 | Miller et al. | |
| 2014/0229955 A1 | 8/2014 | Holmes et al. | |
| 2015/0276775 A1 | 10/2015 | Mellars et al. | |
| 2015/0338427 A1 | 11/2015 | Pollack et al. | |
| 2016/0161516 A1 | 6/2016 | Fritchie et al. | |
| 2016/0341752 A1* | 11/2016 | Holmes | G01N 35/0092 |
| 2018/0080949 A1 | 3/2018 | Jost et al. | |
| 2018/0372648 A1 | 12/2018 | Wissman et al. | |
| 2019/0041318 A1 | 2/2019 | Wissmann et al. | |

FOREIGN PATENT DOCUMENTS

| | | |
|---|---|---|
| WO | 2019126033 | 6/2019 |
| WO | 2019156828 | 8/2019 |
| WO | 2020106693 | 5/2020 |
| WO | 2020106696 | 5/2020 |
| WO | 2021015872 | 1/2021 |
| WO | 2021086550 | 5/2021 |

OTHER PUBLICATIONS

International Search Report for PCT/US2020/036922 dated Aug. 28, 2020.

Sonmez, Reagent usage optimization in high volume diagnostics testing, Massachusetts Institute of Technology, MBA and MS Thesis, Jun. 7, 2018.

Smith Cole J. et al; "A tutorial guide to mixed-inteqer programming models and solution techniques"; University of Florida; Mar. 26, 2007.

Results from the National Survey of Independent and Community Clinical Laboratories, Nov. 14, 2021, by George Washington University.

* cited by examiner

PRIOR ART

FIG. 4A

PRIOR ART

OPTIMIZATION-BASED LOAD PLANNING SYSTEMS AND METHODS FOR LABORATORY ANALYZERS

FIELD

This disclosure relates to systems and methods that provide load planning for laboratory analyzers.

BACKGROUND

Centralization and consolidation of multiple small scale diagnostic laboratories into large scale diagnostic laboratories for the analysis of bio-fluid samples (e.g., blood, urine, etc.) has been a trend in recent years. This trend is driven primarily by reductions in reimbursements by government health insurers for the most frequently ordered laboratory tests. In view of typically small profit margins (e.g., 3%), continued operation by many small scale diagnostic laboratories may not be possible if reimbursement rates continue to drop. Moreover, government reporting requirements for information regarding payer rates and associated test volumes of diagnostic laboratories may necessitate an information technology infrastructure that many small scale diagnostic laboratories do not have the means to implement. Thus, centralization and consolidation of multiple small scale diagnostic laboratories into large scale diagnostic laboratories is likely to continue.

Large scale diagnostic laboratories may process millions of bio-fluid samples each year across a large number of laboratory analyzers (e.g., 100+). The large number of laboratory analyzers may be connected via automated tracks extending, e.g., 200 or more meters. The operation of such large scale diagnostic laboratories requires consistent and continuous monitoring, evaluation, and intervention by human operators to ensure that results are accurate and that service level agreements are satisfied.

Accordingly, there is an unmet need to improve large scale diagnostic laboratories including a large number of laboratory analyzers.

SUMMARY

According to a first aspect, a method of optimization-based load planning for a laboratory analyzer system is provided. The method includes receiving, at a computer server, computer readable data comprising an inventory of a plurality of laboratory analyzers included in the laboratory analyzer system, types and numbers of requested tests to be performed by the laboratory analyzer system, and preferences or priorities related to operation of the laboratory analyzer system and to the types and numbers of requested tests to be performed. The method also includes determining, via an optimization-based load planning module executing on the computer server, a load plan for performing each of the requested tests in the laboratory analyzer system. The load plan comprises computer executable instructions configured to cause a system controller of the laboratory analyzer system to schedule and direct each of the requested tests to be performed at one or more selected laboratory analyzers of the laboratory analyzer system in accordance with one or more of the preferences or priorities.

According to another aspect, a non-transitory computer readable storage medium comprising an optimization-based load planning module having computer executable instructions is provided. The computer executable instructions of the load planning module are configured to cause a computer server to determine a load plan for a laboratory analyzer system comprising a plurality of laboratory analyzers and a system controller. The load plan comprises computer executable instructions configured to cause the system controller to schedule and direct each of a plurality of requested tests to be performed at one or more selected laboratory analyzers of the laboratory analyzer system based on computer readable data received by the computer server. The computer readable data received by the computer server comprises an inventory of the plurality of laboratory analyzers, types and numbers of requested tests to be performed by the laboratory analyzer system, and preferences or priorities related to operation of the laboratory analyzer system and to the types and numbers of requested tests to be performed.

In a further aspect, a laboratory analyzer system is provided. The laboratory analyzer system includes a system controller and a plurality of laboratory analyzers controlled by the system controller and connected to each other via one or more automated tracks for transporting sample containers to and from the plurality of laboratory analyzers. Each of the plurality of laboratory analyzers is configured to perform one or more tests on one or more samples contained in the sample containers. The laboratory analyzer system also includes a computer server coupled to the system controller. The computer server comprises an optimization-based load planning module having computer executable instructions configured to cause the computer server to determine a load plan for the laboratory analyzer system. The load plan comprises computer executable instructions configured to cause the system controller to schedule and direct each of a plurality of requested tests to be performed at one or more selected laboratory analyzers of the laboratory analyzer system based on computer readable data received by the computer server. The computer readable data received by the computer server comprises an inventory of the plurality of laboratory analyzers, types and numbers of requested tests to be performed by the laboratory analyzer system, and preferences or priorities related to operation of the laboratory analyzer system and to the types and numbers of requested tests to be performed.

Still other aspects, features, and advantages of this disclosure may be readily apparent from the following description and illustration of a number of example embodiments and implementations, including the best mode contemplated for carrying out the invention. This disclosure may also be capable of other and different embodiments, and its several details may be modified in various respects, all without departing from the scope of the invention. For example, some embodiments of this disclosure may be applicable to other industries, such as, e.g., aviation, personnel scheduling, and delivery services. This disclosure is intended to cover all modifications, equivalents, and alternatives falling within the scope of the appended claims (see further below).

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Compared to small-scale diagnostic laboratories where only a limited number of laboratory analyzers are used, opportunities to increase efficiency arise with the use of multiple laboratory analyzers that have overlapping test (e.g., assay and/or clinical chemistry) menus. In particular, there is an unmet need to improve operational efficiency of large-scale diagnostic laboratories by creating an optimal assignment of requested tests (e.g., assays and/or clinical chemistry) across the multiple laboratory analyzers. Flexible optimization systems and methods according to embodiments of this disclosure are configured to optimize such lab test assignments across a large number of laboratory analyzers, which may also be referred to as instruments and/or machines (such as immuno-assay instruments, clinical chemistry analyzers, and in vitro analyzers).

Embodiments of the optimization systems and methods may advantageously provide one or more of the following five features: reduced turn-around-time (TAT), load balancing, efficient reagent usage, lower quality assurance costs, and/or improved system robustness. Reducing TAT can increase throughput, staying within limits of service-level agreements, and responding to time-sensitive requests. Providing a balanced load across each laboratory analyzer can improve overall TAT and reduce excessive analyzer wear-out. Reagents may be added to test samples to help determine, measure, or identify a characteristic or condition of the test sample (e.g., measure an amount of glucose or other analyte in a blood sample). Reagents are usually a large cost associated with diagnostic laboratory operations. Thus, optimizing reagent use may be a priority in some laboratory operations. Also, each laboratory analyzer goes through quality control and calibration procedures that incur both time and costs. Thus managing the use of laboratory analyzers for optimal efficiency leads to lower quality assurance costs and time efficiency. And ensuring robustness of the entire laboratory setup increases the likelihood that all requested testing can be completed even in the event of one or more laboratory analyzer being offline, such as for maintenance or repair.

The optimization systems and methods implement the optimization of test assignments across laboratory analyzers as a mixed integer linear program (MILP) that can be tailored to the unique needs of a particular laboratory. For example, if TAT is a desired goal, one or more embodiments of the optimization systems and methods can be configured to prioritize TAT over other considerations. Furthermore, the optimization systems and methods can be utilized continuously to adapt to changing demands of laboratory workloads, such as, e.g., spikes in requests for certain tests.

The optimization systems and methods according to embodiments include configurable constraints and objective functions that can be tailored to the unique needs of a laboratory. Constraints may include, e.g., the number of available reagent pack slots or wedges in a reagent carousel of a laboratory analyzer; initial reagent pack volumes; and configured test menus. Objective functions may include, e.g., quality assurance cost, test assignment redundancy, workload balancing across laboratory analyzers, and a total number visits to laboratory analyzers samples have to make to complete required tests (e.g., some samples may have to visit three or more laboratory analyzers to complete their required testing, while other samples may have to visit only one laboratory analyzer to complete their required testing.

The optimization systems and methods according to embodiments may be configured to find an optimal assignment based on historical data or the current workload of the lab, allow selection of an operation window of the laboratory analyzers based on time or the number of samples to be processed; report assay results and the number of assays that cannot be run to completion because of insufficient reagent; allow easy addition of possible new constraints to an existing system, allow prioritization of objectives with respect to order of importance, relative normalized weights, or a combination of the two; and/or simulate and observe the effects of enabled/disabled constraints and/or objective prioritization on the key performance metrics.

In some embodiments, the optimization systems and methods may provide an extension that can report the required number of reagent packs for each assay so the workload can be run to completion. The optimization systems and methods may additionally or alternatively provide an extension that can predict the expected time when a reagent will run out.

Further details of inventive optimization systems and methods will be described with reference to FIGS. 1-5 herein.

Figure 1:
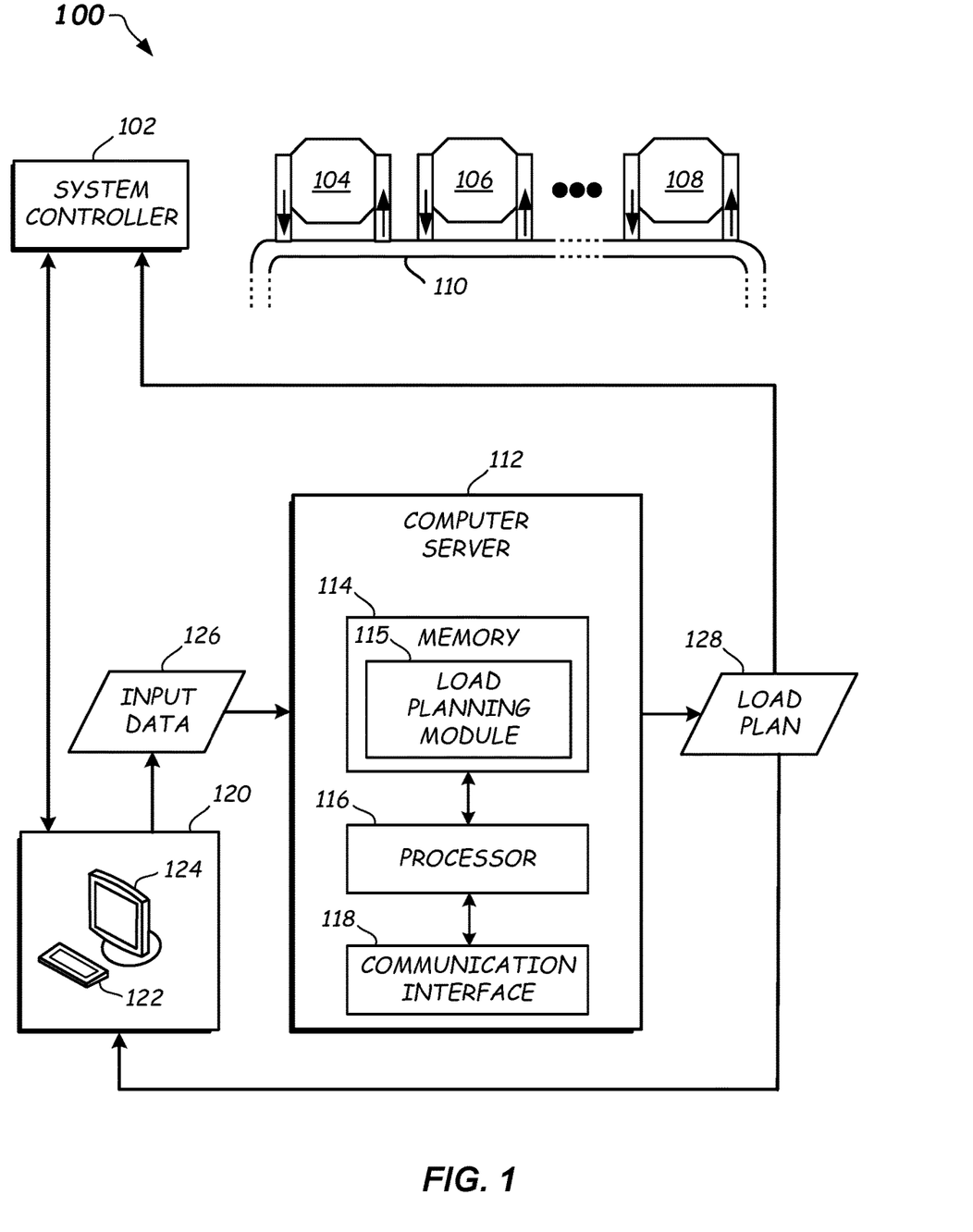
FIG. 1 illustrates a schematic block diagram of a laboratory analyzer system according to one or more embodiments.

FIG. 1 illustrates a laboratory analyzer system 100 according to embodiments. Laboratory analyzer system 100 may automatically process large numbers of biological samples. Laboratory analyzer system 100 may include a system controller 102, a large plurality of laboratory analyzers (represented by laboratory analyzers 104, 106, and 108), one or more automated tracks 110, a computer server 112, and a user interface 120. Laboratory analyzer system 100 may include other components, equipment, and devices (not shown), such as, e.g., various sensors, barcode readers, robotic mechanisms, sample container loading areas, pre-processing stations (which may include, e.g., an automated centrifuge and sample pre-screening equipment), and the like.

Automated track 110 may be configured to transport sample containers (not shown) to and from each of the laboratory analyzers as well as to and from other locations within laboratory analyzer system 100. Sample containers may each be provided with one or more labels that may include identification information thereon, such as, a timestamp, requested test(s), patient identification, etc. The label(s) may include, e.g., a barcode and/or have alphanumeric information printed thereon. The identification information may be machine readable at various locations about laboratory analyzer system 100. Automated track 110 may be a railed track (e.g., a mono rail or a multiple rail), a collection of conveyor belts, conveyor chains, moveable platforms, or any other suitable type of conveyance mechanism. Automated track 110 may be circular or other suitable shape and may be a closed track (e.g., an endless track).

System controller 102 may control the operation of laboratory analyzer system 100 including operation of each laboratory analyzer 104, 106, and 108 for carrying out various types of testing, movement of sample containers to and from each laboratory analyzer 104, 106, and 108 and elsewhere throughout laboratory analyzer system 100, and operation of various other system components (not shown). System controller 102 may include, e.g., a microprocessor-based central processing unit or other suitable processor, a suitable memory, software and/or firmware, and other suitable electronics and hardware for controlling the operation of laboratory analyzer system 100.

Laboratory analyzers 104, 106, and 108 are configured to perform one or more types of diagnostic tests and/or analyses on biological samples, such as, e.g., blood, urine, cerebral-spinal fluid, etc. In some embodiments, laboratory analyzer system 100 may have 100 or more laboratory analyzers, each representing any inventory-consuming diagnostic discipline, such as, e.g., chemistry, immune-assay, hematology, or molecular. In some embodiments, many laboratory analyzers of laboratory analyzer system 100 may be capable of performing the same menu of tests, while other laboratory analyzers may be capable of performing only a limited number of tests or only certain individual tests. Some of the testing performed by the laboratory analyzers of laboratory analyzer system 100 may include, e.g., glucose, Hemoglobin A1C, sodium, potassium, chloride, carbon dioxide, cholesterol, triglyceride, Pro Time, iron, lipase, bilirubin, calcium, magnesium, creatinine, urea nitrogen, thyroid stimulating hormone, hepatitis A, and/or hepatitis B, and the like. Other testing may be performed by the laboratory analyzers of laboratory analyzer system 100.

Figure 2:
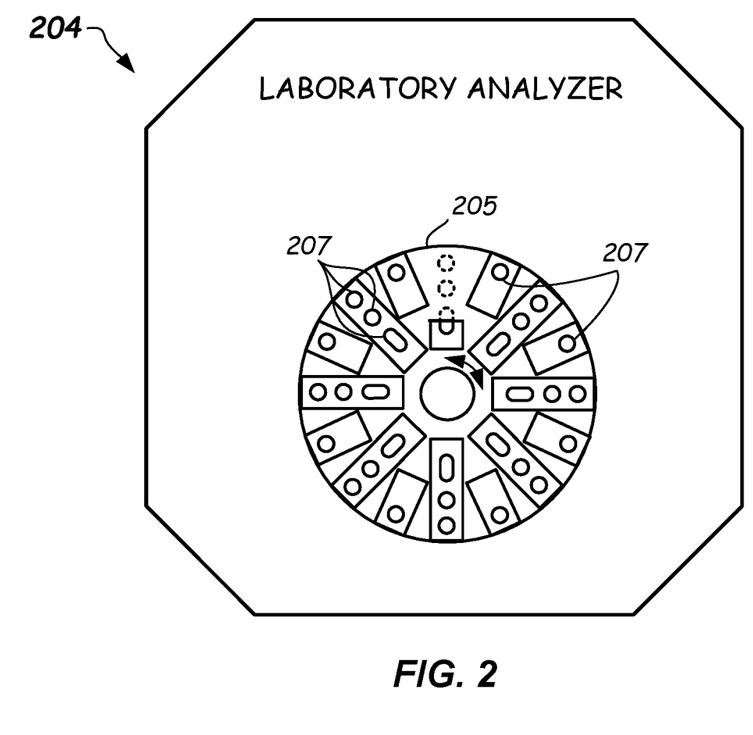
FIG. 2 illustrates a schematic diagram of a laboratory analyzer having a reagent carousel according to one or more embodiments.

As shown in FIG. 2, at least some laboratory analyzers, such as laboratory analyzer 204, include a reagent carousel 205 that has a plurality of reagent slots 207 or locations configured to receive reagents therein. The reagents may be added to test samples to help determine, measure, or identify a characteristic or condition of the test sample (e.g., measure an amount of iron, glucose or other constituent in a blood sample). The reagent slots 207 may be arranged radially around the center of reagent carousel 205 such that a gantry or other robot including a pipette (neither shown) may access any one of the reagents positioned in a reagent slot 207 via rotation of reagent carousel 205. Each of reagent slots 207 may receive a same reagent or a different reagent. The number of slots 207 in reagent carousel 205 may differ across laboratory analyzers.

Returning to FIG. 1, user interface 120 may be communicatively coupled to system controller 102 and to computer server 112. User interface 120 may include a user input device (e.g., keyboard) 122 for entering, e.g., data, requests for status, operational and control commands, etc., to system controller 102 and/or to computer server 112. User interface 120 may also include a display device 124 configured to display status, menus, data, and/or messages received from system controller 102 and computer server 112. For example, user interface 120 may provide information about the operational status of laboratory analyzers 104, 106, and 108 as well as information regarding the status of tests being performed or to be performed thereat.

Computer server 112, which in some embodiments may be cloud based, may be any suitable computer device, and includes a memory 114 (e.g., RAM, ROM, other, or combinations) configured to store programming instructions and other information/data. Computer server 112 may also include a processor 116 (e.g., a CPU, microprocessor, or the like) configured to execute programming instructions. Computer server 112 may further include a communication interface 118 via which computer server 112 may be coupled to and in electronic communication with system controller 102 and user interface 120. In some embodiments, communication interface 118 may enable communication with a network (not shown) coupled between computer server 112 and system controller 102 and/or user interface 120. The network may include, e.g., the Internet, a local area network (LAN), a wireless local area network (WLAN), a power line communication (PLC) network, or the like. Communication interface 118 may be configured to receive input data 126 from user interface 120.

Computer server 112 may also include an optimization-based load planning module 115, described in more detail below. The optimization-based load planning module 115 may be stored in memory 114 and executed by processor 116. In alternative embodiments, the optimization-based load planning module 115 may be stored in other non-transitory computer readable storage mediums. The optimization-based load planning module 115 includes computer executable instructions and may be configured and operable to receive and process input data 126 to create a load plan 128. Input data 126 includes computer readable data representing at least an inventory of the plurality of laboratory analyzers (e.g., laboratory analyzers 104, 106, and 108) included in laboratory analyzer system 100, types and numbers of requested tests to be performed by laboratory analyzer system 100, and preferences or priorities related to operation of laboratory analyzer system 100 and to the types and numbers of requested tests to be performed.

Figure 3:
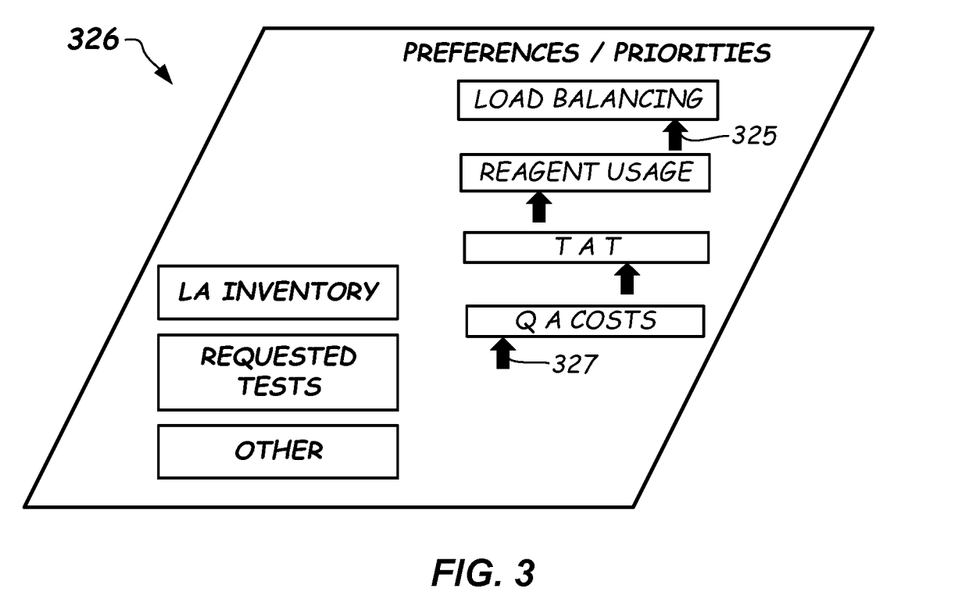
FIG. 3 illustrates a functional block diagram of input data for an optimization-based load planning module according to one or more embodiments.

FIG. 3 illustrates input data 326, which is an embodiment of input data 126 and may be provided as input to optimization-based load planning module 115 in accordance with one or more embodiments. The inventory data of laboratory analyzers (LA Inventory) may indicate, e.g., the total number of available laboratory analyzers, types of tests each laboratory analyzer is capable of performing, and the number of reagent slots for each laboratory analyzer. Other information regarding the laboratory analyzers may additionally or alternatively be included in the inventory data. The requested tests may include requests for testing samples provided to laboratory analyzer system 100 for one or more of the above-listed tests. Other types of tests may be requested, provided that at least one laboratory analyzer is capable of performing the type of test. The preferences or priorities may include at least one of turn-around-time (TAT), load balancing across the laboratory analyzers, reagent usage at the laboratory analyzers, or quality assurance (QA) costs. As shown in FIG. 3, these preferences/priorities may be weighted, wherein an arrow shown to the right side of a particular preference/priority indicates a greater importance, while an arrow shown to the left side of a particular preference/priority indicates a lesser importance. For example, arrow 325 indicates that load balancing is of great importance, while arrow 327 indicates that quality assurance costs are of less importance, in the determination of a particular load plan for laboratory analyzer system 100. Other information regarding the operation of laboratory analyzer system 100 and/or the requested tests to be performed may additionally or alternatively be included in input data 326.

Load plan 128 includes computer executable instructions that may be executed by system controller 102 such that each of the requested tests is performed in laboratory analyzer system 100 in accordance with the objectives (preferences/priorities) received in the input data. More particularly, load plan 128 includes computer executable instructions configured to cause system controller 102 to schedule and direct each of the requested tests to be performed at one or more selected laboratory analyzers (e.g., laboratory analyzers 104, 106, and/or 108) of laboratory analyzer system 100 in accordance with the objectives (preferences/priorities) received in the input data. Load plan 128 may indicate for each selected laboratory analyzer a selected one or more types of tests to be performed thereat, a number of requested tests to be performed thereat, and an order in which the number of requested tests are to be performed.

For example, load plan 128 may provide an assignment of all requested tests to at least a selected sub-plurality of the laboratory analyzers such that each selected laboratory analyzer has a substantially equal number of requested tests to be performed. That is, in some embodiments, no selected laboratory analyzer is assigned, e.g., more than 5%-10% as many tests as a selected laboratory analyzer with the least number of assigned tests.

In another example, load plan 128 may provide an assignment of all requested tests to at least a selected sub-plurality of the laboratory analyzers such that no selected laboratory analyzer is given a number of tests to perform that require more than 5%-10% as much time to complete as a selected laboratory analyzer that first completes all its assigned tests.

In still another example, load plan 128 may provide an assignment of all requested tests to at least a selected sub-plurality of the laboratory analyzers such that each requested test, or each high priority test identified in the input data 126 or 326, is completed within a requested time frame (e.g., 24 hours) or by a specified due date and/or time.

In yet another example, load plan 128 may provide an assignment of all requested tests to at least a selected sub-plurality of laboratory analyzers such that each selected laboratory analyzer has sufficient reagent to perform all requested tests assigned thereto.

The optimization-based load planning module 115 may automatically cause computer server 112 via communication interface 118 to transmit load plan 128 to system controller 102.

Load plan 128 may also or alternatively be viewed and, in some embodiments, edited at user interface 120, and then transmitted to system controller 102 by a human operator. User interface 120 is configured to facilitate interactions between a human operator and the optimization-based load planning module 115. In particular, input device 122 and display device 124 may be operative to display a menu including icons, scroll bars, boxes, and/or buttons through which the human operator may interface with the optimization-based load planning module 115 to, e.g., enter input data 126 or 326, view a variety of control and status display screens, and/or view, edit, and/or forward to system controller 102 load plan 128. In some embodiments, the control and status display screens may display and enable control of some or all aspects of the optimization-based load planning module 115.

In some embodiments, the optimization-based load planning module 115 may be implemented using mixed integer linear programming. As described above, the optimization-based load planning module 115 receives input data 126 or 326. Input data 126 or 326 may include, additionally or alternatively to the types of input data described above, a time-window of the samples to be considered by the optimization-based load planning module 115. Given a day's workload of samples to be tested, the optimization-based load planning module 115 may include only samples that fall within the time-window or only up to a certain number of samples. In some embodiments, a presumption of the optimization-based load planning module 115 is that a reagent slot 207 (FIG. 2) once loaded with a reagent pack is not reloaded during the optimization window. Thus, the maximum number of tests that can be run on a laboratory analyzer may depend on the number of initial reagent packs loaded therein, their volumes, and per unit volume consumed by each corresponding test. This information may be included in the inventory data of input data 126 or 326. The optimization-based load planning module 115 may be configured to create an assignment of requested tests based on the available reagents in the laboratory analyzers and one or more of the following five user-selected objectives (each of which may also be weighted relative to the others by the user): reduced turn-around-time (TAT), load balancing, efficient reagent usage, lower quality assurance costs, and/or improved system robustness.

In some embodiments, the following algorithm may be used to implement the optimization-based load planning module 115 (note that the terms "laboratory analyzer," "instrument," and "machine" are used interchangeably; and that the terms "reagent slot" and "wedge" are used interchangeably):

Let $x_{ijw}$ denote a binary decision variable which indicates the assignment of test $j \in T$ to laboratory analyzer $i \in M$ on wedge $w \in W$ where T, M and W represent the sets of tests, machines, and wedges, respectively:

$$x_{ijw} = \begin{cases} 1, & \text{if instrument } i \text{ has test } j \text{ loaded} \\ & \text{in the } w\text{th wedge (reagent container),} \\ 0, & \text{otherwise.} \end{cases}$$

The notation $S \in \{0, 1\}^{|A| \times |T|}$ is defined as a binary matrix encoding the required tests for each sample:

$$S_{aj} = \begin{cases} 1, & \text{if sample } a \text{ requires test } j, \\ 0, & \text{otherwise.} \end{cases}$$

where $a \in A$, $j \in T$, and A is the set of all patient samples.

Given the sample data S, an optimal loading plan corresponds to solving a mixed integer program that optimizes objectives under equipment and testing related constraints:

minimize $f(x_{ijw})$ subject to $g(x_{ijw,S}) \geq 0$, $x_{ijw} \in \{0, 1\}$, where f and g are composite functions of objectives and constraints respectively. Table 1 below lists all related variables for quick reference.

TABLE 1

Variable list involved in the optimization process

| Variable Name | Definition | Type |
|---|---|---|
| $x_{ijw}$ | 1 if instrument i has test j loaded in the w-th wedge (reagent container) | Optimization |
| $n_{ij}$ | Total number of test j that will be processed on instrument i | Optimization |
| $\epsilon_j$ | Slack variable indicating the total number of uncompleted test j due to unmet capacity | Optimization |
| $I_{ai}$ | 1 if instrument i can be used to cover a test or tests requested by sample α | Optimization |

TABLE 1-continued

Variable list involved in the optimization process

| Variable Name | Definition | Type |
|---|---|---|
| $r_j$ | Volume of consumed reagent for performing one test j (instrument independent) | Input Data |
| $q_j$ | Unified quality assurance related costs of test j | Input Data |
| $m_j$ | Minimum number of instruments to perform test j on | Input Data |
| $RE_j$ | Redundancy factor of test j indicating the relative need to run it on multiple instruments | Input Data |
| $V_{ijw}$ | Initial reagent pack size (volume) of test j placed in instrument i on wedge w | Input Data |
| $S_{\alpha j}$ | 1 if sample $\alpha$ requires test j | Input Data |

Optimization Objectives

In some embodiments, the objectives to be optimized may include: quality assurance (QA) cost, test assignment redundancy, workload balancing across instruments, and the total number of instrument visits samples have to make to complete the required tests. An indicator function can be defined as $I: \mathbb{Z}_+^{N \times J} \to \{0, 1\}^{N \times J}$. Here $\mathbb{Z}_+$ refers to the set of all non-negative integers. For any matrix $M \in \mathbb{Z}_+^{N \times J}$, $I(M_{ij})=1$ if $M_{ij} \geq 0$ and $I(M_{ij})=0$ otherwise. This indicator function may be useful in identifying the tests that are loaded in the laboratory analyzer system. For example, a frequently used notation $I(\Sigma_{w \in W} x_{ijw})$ sums over all the wedges in instrument i and thus indicates if a test j is present on it. In matrix form, over all instruments and tests, the following can be provided:

$$\left\{ I\left( \sum_{w \in W} x_{ijw} \right) \right\}_{ij} = \begin{cases} 1, & \text{if instrument } i \text{ loaded test } j \text{ (in any wedge)}, \\ 0, & \text{otherwise}. \end{cases}$$

The mathematical formulations of the optimization objectives are given in more detail below:

1) Objective function to minimize the quality assurance (QA) costs:

$$C_{QA} = \sum_{i \in M} \sum_{j \in \mathcal{T}} q_j I\left( \sum_{w \in W} x_{ijw} \right).$$

where $q_j$ is the unified cost of QA material cost, reagent cost, and costs associated with downtime. For each laboratory analyzer, the QA cost increases as the laboratory analyzer loads more different types of tests.

2) Objective function to minimize the unmet capacity cost: Given that the workload and amount of resources, such as loaded reagent volume, might not suffice to process all the samples, the number of uncompleted tests of assay j is denoted as $\epsilon_j$ and the unmet capacity cost is stated as follows:

$$C_{MC} = \sum_{j \in \mathcal{T}} \epsilon_j$$

An optimality condition for this objective is $\Sigma_{j \in \mathcal{T}} \epsilon_j = 0$, meaning all the tests can be processed within the given resources.

3) Objective function to maximize test assignment redundancy: Consider the scenario where it is preferable to perform particular test/tests on several machines for robustness and assume that a redundancy factor $RE_j > 0$ is provided, for example, within the input data. The objective function then measures the total redundancy achieved by the test assignment:

$$C_R = \sum_{j \in \mathcal{T}} RE_j \sum_{i \in M} I\left( \sum_{w \in W} x_{ijw} \right).$$

Here $\Sigma_{i \in M} I(\Sigma_{w \in W} x_{ijw})$ is the number of instruments that load test j. Maximizing this objective will encourage tests with large redundancy factors to be assigned to more than one instrument.

4) Objective function to minimize for workload balancing: A balanced distribution of samples and tests across laboratory analyzers is needed to achieve optimal TAT and reduce excessive wear-out. Two strategies are identified to achieve this task as each has its own merits. The optimization-based load planning module 115 allows a combination of these two approaches. A first strategy in achieving load balancing strives for equal distribution of the total amount of an assay (testing) across the instruments the assay would be performed on. To do so, the deviation of $n_{ij}$, assigned number of test js on laboratory analyzer i, is penalized from a nominal value. This nominal value is selected for each test to be the following average:

$$\hat{n}_j^{avg} = \frac{\sum_{a \in \mathcal{A}} S_{aj}}{\hat{N}_j}$$

where $\hat{N}_j$ is the number of instruments having test j assigned. However, the computation of this nominal value requires the knowledge of $\hat{N}$, which can only be obtained by solving another optimization problem. To untangle this dependence, a surrogate, $N_j$, is used, defined as the number of instruments that has test j enabled on its test menu. Since $\hat{N}_j \leq N_j$, we obtain a lower bound to the nominal value, $n_j^{avg}$, such that $n_j^{avg} \leq \hat{n}_j^{avg}$, This objective function can then be written as follows:

$$C_{LB,A} = \sum_{i \in M} \sum_{j \in \mathcal{T}} (n_j^{avg} - n_{ij})^2.$$

A second approach in achieving load balancing strives for equal distribution of the total number of tests to be performed on each laboratory analyzer regardless of the test type. Similar to the first strategy, the deviation from a nominal value is sought to be minimized. In this case, the nominal value is defined as follows:

$$\hat{n}^{avg} = \frac{\sum_{i \in M} \sum_{j \in \mathcal{T}} n_{ij}}{|M|}$$

However, as $n_{ij}$ are optimization variables and, thus, the nominal value is not known in advance. Instead, a surrogate is used:

$$n^{avg} = \frac{\sum_{a \in \mathcal{A}} \sum_{j \in \mathcal{T}} S_{aj}}{|\mathcal{M}|}$$

This surrogate is an upper bound such that $n^{avg} \leq \hat{n}_j^{avg}$ as not all the tests might be completed with the available reagent volumes. The objective function is then:

$$C_{LB,S} = \sum_{i \in \mathcal{M}} \left( n_j^{avg} - \sum_{j \in \mathcal{T}} n_{ij} \right)^2.$$

Then the overall load balancing objective can be written as follows:

$$C_{LB} = \beta_1 C_{LB,A} + \beta_2 C_{LB,S},$$

where $\beta_1$ and $\beta_2$ are non-negative weights adjusting the relative contribution of each balancing strategy.

Unlike the previous objective functions, the load balancing cost function is quadratic. Inclusion of such objectives to the formulation significantly increases the computational burden as the problem becomes an instance of mixed integer quadratic programming. This is tackled by measuring and minimizing the linear deviation from the nominal values through the use of integer non-negative slack variables for both $C_{LB,A}$ and $C_{LB,S}$. In linearizing $C_{LB,A}$, $n_+^{ij}$ and $n_-^{ij}$ are used as slack variables corresponding to the excess and missing load of test j on instrument i:

minimize $\Sigma_{i \in M} \Sigma_{j \in T}(n_-^{ij} + n_+^{ij})$ subject to $n_{ij} = n_{avg}^j + n_+^{ij} - n_-^{ij}$, $n_+^{ij} \geq 0, n_-^{ij} \geq 0$.

Linearization of $C_{LB,S}$ follows a very similar approach with the introduction of slack variables and is left out for conciseness.

5) Objective function to minimize the total laboratory analyzer visits to be made by the samples: Each sample generally requires multiple laboratory analyzer visits. This is due to the assay menu differences on the same types of laboratory analyzers or the need to visit different types of laboratory analyzers. Each such laboratory analyzer visit of a sample affects the sample's TAT along with the overall TAT. This phenomenon may be accounted for by counting the number of total stops samples are required to make:

$$C_{stops} = \sum_{a \in \mathcal{A}} \sum_{i \in \mathcal{M}} I_{ai}$$

where $I_{ai}$ is a binary variable indicating whether sample "a" will require instrument i:

$$I_{aj} = \begin{cases} 1, & \text{if sample } a \text{ requires instrument } i, \\ 0, & \text{otherwise.} \end{cases}$$

Minimizing this objective will encourage sample "a" to request as few instruments as possible, and thus reduces the number of stops it makes, directly optimizing TAT.

Optimization Constraints

The mathematical formulation of the optimization constraints is now described. The optimization constraints are closely related to the factors that affect the throughput of the labs: number of available reagent slots (wedges) in the laboratory analyzers, initial reagent pack volumes, and configured test menu. A feasible solution should satisfy all these constraints. The formulation of each optimization constraint is now detailed.

1) A reagent slot cannot be assigned more than one assay:

$\Sigma_j x_{ijw} \leq 1, \forall w \in W, i \in M$.

Note that in the case where each laboratory analyzer has a different number of reagent slots, the formulation can be trivially modified to define a set of reagent slots (wedges) $W_i$ for each laboratory analyzer (instrument) i.

2) Number of reagent packs to load cannot be greater than the number reagent slots in the laboratory analyzer:

$0 \leq \Sigma_{j \in T} I(\Sigma_{w \in W} x_{ijw}) \leq |W|, \forall i \in M$.

3) All types of requested tests must be covered: This constraint ensures that for each requested test there is at least one laboratory analyzer to perform it:

$I(\Sigma_{a \in A} S_{aj}) \leq I(\Sigma_{i \in M} I(\Sigma_{w \in W} x_{ijw})) \forall j \in T$.

This constraint induces J inequalities. For simplicity, the notation I is abused here to refer to a generic element-wise indicator function. Given a fixed test type j, $I(\Sigma_{a \in A} S_{aj}) \in \{0,1\}$ is a binary variable indicating whether test j is ordered by the samples. The right hand side of this constraint, $I(\Sigma_{I \in M} I(\Sigma_{w \in W} x_{ijw})) \in \{0,1\}$, indicates whether there exists an instrument that has test j assigned. The inequality used in this constraint indicates that for each requested test j, there is at least one laboratory analyzer to perform it.

4) All requested tests should be completed: This constraint is directly related to the second objective function, $C_{MC}$ defined above in the Optimization Objectives section and ensures that tests are completed as much as possible. The possibility of uncompleted samples due to capacity or time-frame issues is accounted for by using the slack variable $\epsilon_j$ for each test j. The constraint then becomes:

$\Sigma_{i \in M} n_{ij} + \epsilon_j a_{a \in A} S_{aj}, \forall j \in T$, with $n_{ij} \geq 0, \epsilon_j \geq 0, \forall i \in M, j \in T$.

5) Laboratory analyzer (instrument) i is not allowed to run test j if that test is not enabled (or does not exist in the test menu): This constraint indeed includes two scenarios. First, test j is included in the factory system menu of the laboratory analyzer i but not turned on, then the reagent slots of this laboratory analyzer should not be assigned test j. Second, test j does not exist in the factory system menu of the laboratory analyzer. This is the case when test j falls in a different category with the laboratory analyzer. For example, a chemistry test cannot be performed on an immunoassay analyzer. Both scenarios are considered in this constraint:

$$\begin{cases} n_{ij} \geq 0, & \text{if instrument } i \text{ is configured/} \\ & \text{allowed to run test } j, \\ n_{ij} = 0, & \text{otherwise.} \end{cases}$$

6) The reagent volume of the performed tests should be less than the total volumes stored in the reagent slots of the laboratory analyzers, $n_{ij} r_{ij} \leq \Sigma_{w \in W} x_{ijw} V_{ijw} \forall i \in M, j \in T$, where $V_{ijw}$ is the container size (volume) in laboratory analyzer (instrument) i for test j on reagent slot (wedge) w. As reloading of reagents during the optimization window is not considered, the maximum number of tests that can be run on the instruments will depend on the initial volumes of the reagent packs.

7) Redundancy constraints: This constraint complements the objective function maximizing the total redundancy factor described in the Optimization Objectives section above by explicitly enforcing a minimum number of laboratory analyzers, $m_j$, running test j:

$$\Sigma_{i \in M} I(\Sigma_{w \in W} x_{ijw}) \geq m_j \ \forall \ j \in T.$$

The expression, $I(\Sigma_{w \in W} x_{ijw}) \in \{0,4\}$ indicates whether the instrument i is assigned test j in any of its wedges. The $\Sigma_{i \in M} I(\Sigma_{w \in W} x_{ijw})$ counts for the total number of laboratory analyzers that has test j assigned.

8) Number of stops related constraints: In minimizing the number of total stops made by all the samples as given in an objective, a requirement is that there is at least one set of machines to perform the requested tests. The set of tests requested by sample a is denoted by $R_a = \{j | S_{aj} > 0, j \in T\}$ and the set of instruments that has test j assigned is denoted by $K_j = \{i | I(\Sigma_{w \in W} x_{ijw}) > 0, i \in M\}$. Then, the cover constraint can be written as follows:

$$\Sigma_{j \in R_a} \Sigma_{i \in K_j} I_{ai} \geq 1, \ \forall a \in A.$$

Note here that the term $\Sigma_{i \in K_j} I_{ai}$ is a non-linear combination (multiplication) of two indicator variables, $I(\Sigma_{w \in W} x_{ijw})$ and $I_{ai}$, that are both tied to the optimization variables $x_{ijw}$. This non-linearity imposes additional computational complexity and to alleviate this, this combination is relaxed by introducing an additional binary slack variable $II_{aij}$ and transforming the original constraints into following:

$$\sum_{j \in R_a} \sum_{i \in M} II_{aij} \geq 1, \ \forall \ a \in \mathcal{A},$$

$$\text{subject to } II_{aij} \leq I\left(\sum_{w \in W} x_{ijw}\right),$$

$$II_{aij} \leq I_{ai},$$

$$II_{aij} \geq I\left(\sum_{w \in W} x_{ijw}\right) + I_{ai} - 1.$$

Optimization Strategies

As described above, objectives and constraints can be configured with respect to the needs of a laboratory analyzer system. For example, the redundancy factors of assays or minimum number of laboratory analyzers to use in assigning an assay can be tailored for the lab based on historical data or operational considerations. Similarly, objectives can be prioritized based on specific needs as, in general, each of the objectives cannot be optimized simultaneously to each of their individual best value, because they may be contradicting. In such cases, for example, it is impossible to find a solution where the objective due to QA cost is minimized, while the assignment redundancy objective is maximized. The concept of optimality in multi-objective optimization can be characterized by what is called Pareto optimality.

Given k objective functions, $\mathcal{C}_1, \mathcal{C}_2, \ldots, \mathcal{C}_k$, a solution x* is Pareto-optimal if and only if there exists no other solution x such that $\mathcal{C}_i(x) < \mathcal{C}_i(x^*), \ \forall \ i \in \{1, \ldots, k\}$.

In a Pareto-optimal assignment, a particular objective or objectives cannot be improved without incurring an additional loss or losses from other objective(s). It is what the optimization can do best in a multi-objective problem. For example, this might correspond to an assignment where a workload balancing objective cannot be reduced without degrading the objective function for QA costs. In this assay assignment problem, returning assignments from this set of Pareto-optimal solutions is of interest.

Two approaches are used to reach Pareto optimal solutions: lexicographic and weighted-sum. The lexicographic solution method is useful when a specific order of importance of the objectives exists. The lexicographic approach can be applied by solving the optimization problem sequentially with the objective in the order of importance, together with requirements, on the set of possible solution as described in the Optimization Constraints section above. Given a set of ordered objectives, the lexicographic approach proceeds as follows:

1) Construct an optimization problem including variables and constraints associated with requirements;
2) for i=1, . . . , k do
3) Minimize $C_i(x)$;
4) x*←the optimal solution;
5) if i<k then
6) Add a constraint $\mathcal{C}_i(x) \leq \mathcal{C}_i(x^*)$;
7) Return x*;

The second method in finding Pareto-optimal solutions is the weighted-sum approach. Given weights $w_1, w_2, \ldots, w_k \in \mathbb{R}^+,$, corresponding to each objective, the optimization problem is solved with a single objective function as follows:

$$\text{Minimize } W_1 \mathcal{C}_{QA} + w_2 \mathcal{C}_{MC} - w_3 \mathcal{C}_R + w_4 \mathcal{C}_{LB} + w_5 \mathcal{C}_{stops}$$

In general, the most viable option for many diagnostic laboratories would be to use a combination of the lexicographic and weighted-sum approaches as a strict ordering of objectives might not necessarily exist. In such cases, some objectives can have the same lexicographic order and thus be optimized together with associated weights. The optimization-based load planning module 115 can employ all of these optimization approaches.

Figure 4A:
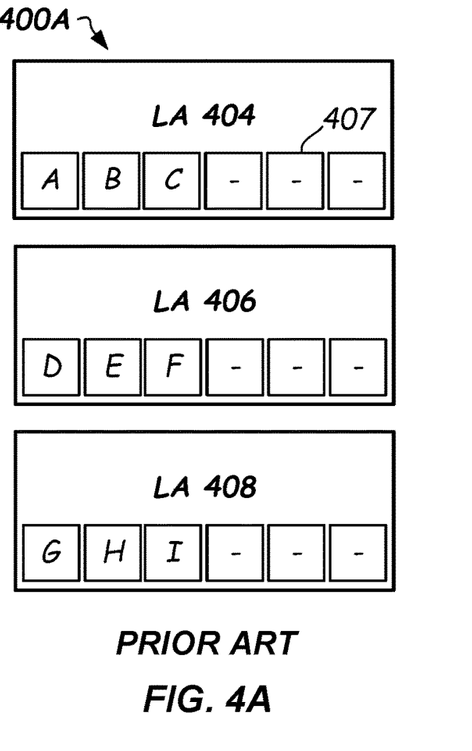
FIGS. 4A-B illustrate example load plans for a laboratory analyzer system according to the prior art.
Figure 4B:
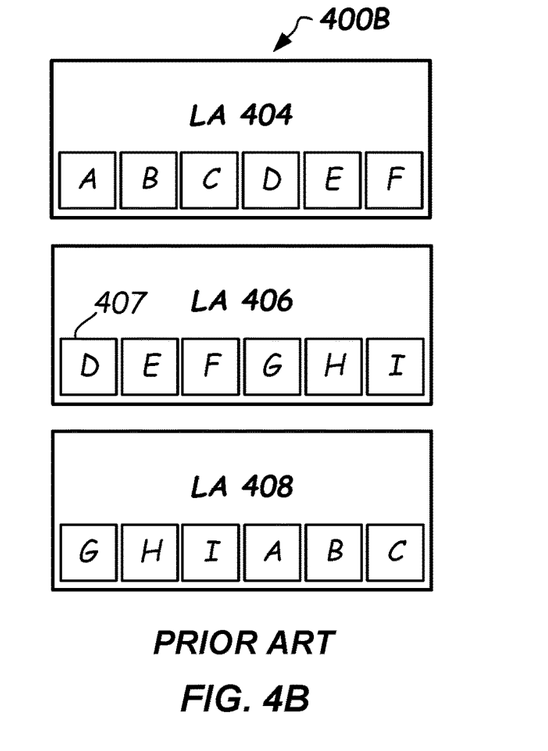
Figure 4C:
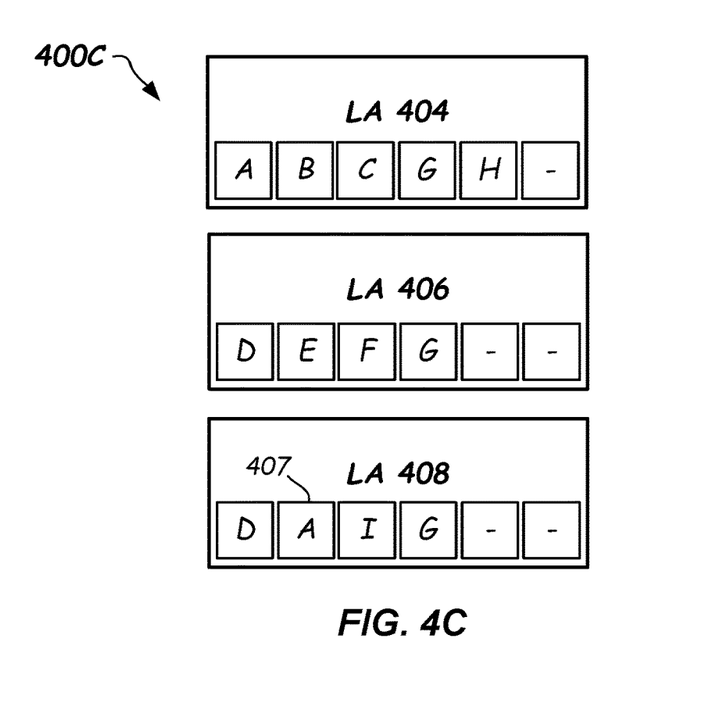
FIG. 4C illustrates an example load plan for a laboratory analyzer system according to one or more embodiments.

FIGS. 4A and 4B illustrate examples of load plans 400A and 400B that may be created conventionally, while FIG. 4C illustrates an example of a load plan 400C that may be created by the optimization-based load planning module 115 according to one or more embodiments. Each of the load plans 400A, 400B, and 400C are based on the same set of objectives and constraints for a laboratory analyzer system offering a menu of nine types of immunoassay tests: A, B, C, D, E, F, G, H, and I, wherein tests A and G are frequently requested together. The laboratory analyzer system has three laboratory analyzers 404, 406, and 408, each having six reagent slots 407 (only one labeled in each of FIGS. 4A-C). Each of the reagent slots 407 may be loaded with a particular reagent pack to be used for one of the nine types of tests. The objectives are load balancing, reagent usage, quality assurance costs, and system robustness (e.g., sufficient redundancy to overcome a laboratory analyzer failure).

As shown in FIG. 4A, conventional load plan 400A may evenly distribute the nine tests across the three laboratory analyzers 404, 406, and 408, such that each performs a different set of three tests: laboratory analyzer 404 performs tests A, B, and C; laboratory analyzer 406 performs tests D, E, and F; and laboratory analyzer 408 performs tests G, H, and I. A problem may result, however, if any one of laboratory analyzers 404, 406, and/or 408 fails. The tests assigned to the failed laboratory analyzer cannot be performed at either of the other two operating laboratory analyzers, as load plan 400A has no redundancy. Furthermore, any sample requiring tests A and G has to visit both laboratory analyzers 404 and 408, which may degrade system throughput and turn-around-time (TAT).

FIG. 4B shows conventional load plan 400B, which is based on redundancy. Each of laboratory analyzers 404, 406, and 408 performs a different combination of six tests: laboratory analyzer 404 performs tests A, B, C, D, E, and F; laboratory analyzer 406 performs tests D, E, F, G, H, and I; and laboratory analyzer 408 performs tests G, H, I, A, B, and C. However, load plan 400B results in double the reagent costs, as each test is performed in two laboratory analyzers, and twice the quality assurance costs, as each laboratory analyzer (performing six types of tests) requires twice as much calibration and quality control as load plan 400A (wherein each laboratory analyzer performs only three types of tests).

FIG. 4C shows load plan 400C created by the optimization-based load planning module 115 according to embodiments. Load plan 400C distributes the testing across laboratory analyzers 404, 406, and 408 such that each analyzer performs only five or four tests, thus achieving load balance and reducing quality assurance costs. That is, laboratory analyzer 404 performs tests A, B, C, G, and H; laboratory analyzer 406 performs tests D, E, F, and G; and laboratory analyzer 408 performs tests D, A, I, and G. Moreover, tests A and G, commonly requested together, are both performed at two of the three laboratory analyzers (laboratory analyzers 404 and 408), thus reducing the number of visits to laboratory analyzers per sample, which in turn may increase throughput and/or turn-around-time. Downtime exposure due to analyzer failure is also reduced because three of the nine types of tests (A, D, and G) are performed in at least two of the three laboratory analyzers. And load plan 400C results in lower reagent costs as all slots 407 are not used (and loaded with reagent packs).

Figure 5:
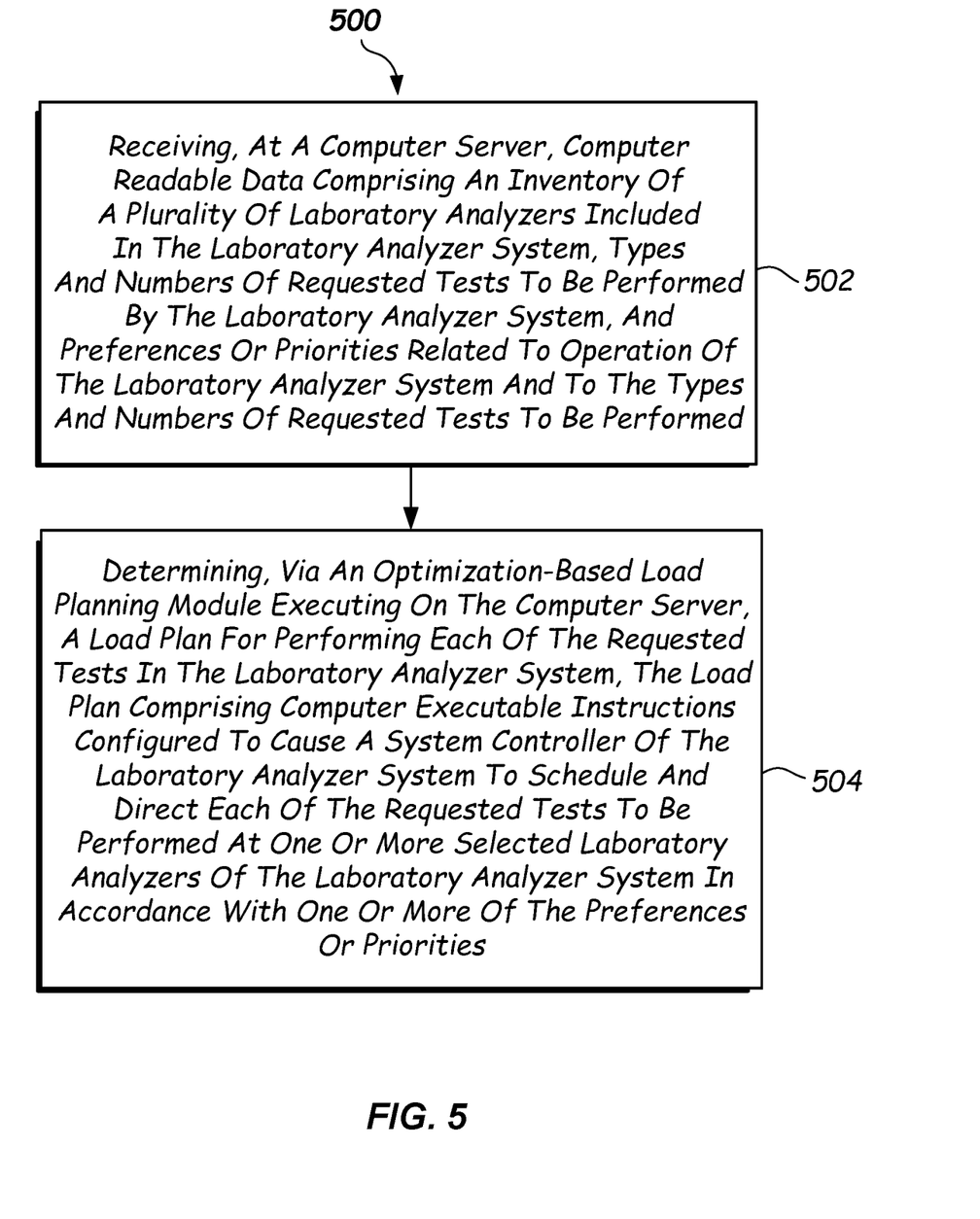
FIG. 5 is flowchart of a method of optimization-based load planning for a laboratory analyzer system according to one or more embodiments.

FIG. 5 illustrates a flowchart of a method 500 of optimization-based load planning for a laboratory analyzer system according to one or more embodiments of the disclosure. Method 500 may be carried out by a suitable computer server, such as, e.g., computer server 112, a suitable system controller, such as, e.g., system controller 102, or other suitable computer device. Method 500 may include, at process block 502, receiving, at a computer server, computer readable data comprising an inventory of a plurality of laboratory analyzers included in a laboratory analyzer system, types and numbers of requested tests to be performed by the laboratory analyzer system, and preferences or priorities related to operation of the laboratory analyzer system and to the types and numbers of requested tests to be performed. For example, the computer readable data may represent input data 126 of FIG. 1 or input data 326 of FIG. 3.

Method 500 may also include, in process block 504, determining, via an optimization-based load planning module executing on the computer server, a load plan for performing each of the requested tests in the laboratory analyzer system. The load plan may comprise computer executable instructions configured to cause a system controller of the laboratory analyzer system to schedule and direct each of the requested tests to be performed at one or more selected laboratory analyzers of the laboratory analyzer system in accordance with one or more of the preferences or priorities. In some embodiments, the optimization-based load planning module may be optimization-based load planning module 115, the load plan may be load plan 128, the system controller may be system controller 102, the laboratory analyzers may be laboratory analyzers 104, 106, and 108, and/or the laboratory analyzer system may be laboratory analyzer system 100 all of FIG. 1.

In some embodiments, the load plan may include computer executable instructions indicating assignment of all requested tests to at least some selected laboratory analyzers such that each selected laboratory analyzer has a substantially equal number of requested tests to be performed. In other embodiments, the load plan may include computer executable instructions indicating assignment of all requested tests to at least some selected laboratory analyzers such that each selected laboratory analyzer has sufficient reagent to perform all requested tests assigned thereto.

In one or more embodiments, method 500 may further include transmitting the load plan from the computer server to the system controller of the laboratory analyzer system, wherein the load plan is executed by the system controller to schedule and direct each of the requested tests to be performed at one or more selected laboratory analyzers of the laboratory analyzer system in accordance with one or more of the preferences or priorities.

While the disclosure is susceptible to various modifications and alternative forms, specific method and system embodiments have been shown by way of example in the drawings and are described in detail herein. It should be understood, however, that the particular methods and systems disclosed herein are not intended to limit the disclosure but, to the contrary, to cover all modifications, equivalents, and alternatives falling within the scope of the claims.

What is claimed is:

1. A method of optimization-based load planning for a laboratory analyzer system, comprising:
   receiving, at a computer server, computer readable data comprising an inventory of a plurality of laboratory analyzers included in the laboratory analyzer system, types and numbers of requested tests to be performed by the laboratory analyzer system, and preferences or priorities related to operation of the laboratory analyzer system and to the types and numbers of requested tests to be performed;
   determining, via an optimization-based load planning module executing on the computer server, a load plan for performing each of the requested tests in the laboratory analyzer system, the load plan comprising computer executable instructions configured to cause a system controller of the laboratory analyzer system to schedule and direct each of the requested tests to be performed at one or more selected laboratory analyzers of the laboratory analyzer system in accordance with one or more of the preferences or priorities; and
   scheduling and directing, via the system controller executing the computer executable instructions of the load plan, each of the requested tests to be performed at one or more selected laboratory analyzers of the laboratory analyzer system in accordance with the one or more of the preferences or priorities.

2. The method of claim 1, further comprising transmitting the load plan to the system controller of the laboratory analyzer system.

3. The method of claim 1, wherein the inventory of the plurality of laboratory analyzers indicates a number of laboratory analyzers, types of tests each laboratory analyzer is capable of performing, and a number of reagent slots for each laboratory analyzer.

4. The method of claim 1, wherein the types of requested tests to be performed include at least one of glucose, cholesterol, iron, lipase, bilirubin, calcium, magnesium, or creatinine.

5. The method of claim 1, wherein the preferences or priorities include at least one of turn-around-time, load balancing across the laboratory analyzers, reagent usage at the laboratory analyzers, or quality assurance costs.

6. The method of claim 1, wherein the load plan comprising computer executable instructions indicates for at least some selected laboratory analyzers a selected one or more types of tests to be performed thereat, a number of requested tests to be performed thereat, and an order in which the number of requested tests are to be performed.

7. The method of claim 1, wherein the load plan comprising computer executable instructions indicates an assignment of all requested tests to at least some selected laboratory analyzers such that each selected laboratory analyzer has a substantially equal number of requested tests to be performed.

8. The method of claim 1, wherein the load plan comprising computer executable instructions indicates an assignment of all requested tests to at least some selected laboratory analyzers such that each selected laboratory analyzer has sufficient reagent to perform all requested tests assigned thereto.

9. A non-transitory computer readable storage medium comprising a load plan of computer executable instructions configured to cause a system controller of a laboratory analyzer system to:
schedule and direct each of a plurality of requested tests to be performed at one or more selected laboratory analyzers of the laboratory analyzer system based on computer readable data received and processed by a computer server to create the load plan, the computer readable data comprising an inventory of the plurality of laboratory analyzers, types and numbers of requested tests to be performed by the laboratory analyzer system, and preferences or priorities related to operation of the laboratory analyzer system and to the types and numbers of requested tests to be performed.

10. The non-transitory computer readable storage medium of claim 9, wherein the computer executable instructions of the load plan include an order in which the requested tests are to be scheduled and directed to be performed by the system controller.

11. The non-transitory computer readable storage medium of claim 9, wherein the inventory of the plurality of laboratory analyzers indicates a number of laboratory analyzers, types of tests each laboratory analyzer is capable of performing, and a number of reagent slots for each laboratory analyzer.

12. The non-transitory computer readable storage medium of claim 9, wherein the load plan indicates an assignment of all requested tests to at least some selected laboratory analyzers such that each selected laboratory analyzer has a substantially equal number of requested tests to be performed.

13. The non-transitory computer readable storage medium of claim 9, wherein the load plan indicates an assignment of all requested tests to at least some selected laboratory analyzers such that each selected laboratory analyzer has sufficient reagent to perform all requested tests assigned thereto.

14. The non-transitory computer readable storage medium of claim 9, wherein the plurality of requested tests to be performed include at least one of glucose, cholesterol, iron, lipase, bilirubin, calcium, magnesium, or creatinine.

15. A laboratory analyzer system, comprising:
a system controller;
a plurality of laboratory analyzers controlled by the system controller and connected to each other via one or more automated tracks for transporting sample containers to and from the plurality of laboratory analyzers, each of the plurality of laboratory analyzers configured to perform one or more tests on one or more samples contained in the sample containers; and
a computer server coupled to the system controller, the computer server comprising an optimization-based load planning module having computer executable instructions configured to cause the computer server to determine a load plan for the laboratory analyzer system, wherein the load plan comprises computer executable instructions configured to cause the system controller to schedule and direct each of a plurality of requested tests to be performed at one or more selected laboratory analyzers of the laboratory analyzer system based on computer readable data received by the computer server, the computer readable data comprising an inventory of the plurality of laboratory analyzers, types and numbers of requested tests to be performed by the laboratory analyzer system, and preferences or priorities related to operation of the laboratory analyzer system and to the types and numbers of requested tests to be performed; wherein:
the system controller, executing the computer executable instructions of the load plan, schedules and directs each of the plurality of requested tests to be performed at the one or more selected laboratory analyzers of the laboratory analyzer system in accordance with the load plan.

16. The laboratory analyzer system of claim 15, wherein at least some of the laboratory analyzers have a reagent carousel.

17. The laboratory analyzer system of claim 15, wherein the inventory of the plurality of laboratory analyzers indicates a number of laboratory analyzers, types of tests each laboratory analyzer is capable of performing, and a number of reagent slots for each laboratory analyzer.

18. The laboratory analyzer system of claim 15, wherein the preferences or priorities include at least one of turn-around-time, load balancing across the plurality of laboratory analyzers, reagent usage at the laboratory analyzers, or quality assurance costs.

19. The laboratory analyzer system of claim 15, wherein the load plan indicates an assignment of all requested tests to at least some selected laboratory analyzers such that each selected laboratory analyzer has a substantially equal number of requested tests to be performed.

20. The laboratory analyzer system of claim 15, wherein the load plan indicates an assignment of all requested tests to at least some selected laboratory analyzers such that each selected laboratory analyzer has sufficient reagent to perform all requested tests assigned thereto.

* * * * *